(12) United States Patent
Weiss et al.

(10) Patent No.: US 8,527,065 B2
(45) Date of Patent: Sep. 3, 2013

(54) ELECTRODE DEVICE FOR ACTIVE MEDICAL IMPLANT

(75) Inventors: Ingo Weiss, Berlin (DE); Michael Friedrich, Kleinmachnow (DE); Stefan Knorr, Berlin (DE); René Fischer, Berlin (DE); Marc Steffen Schurr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 212 days.

(21) Appl. No.: 13/018,198

(22) Filed: Jan. 31, 2011

(65) Prior Publication Data

US 2011/0196462 A1    Aug. 11, 2011

(30) Foreign Application Priority Data

Feb. 11, 2010   (DE) .................. 10 2010 000 372

(51) Int. Cl.
*A61N 1/00* (2006.01)
(52) U.S. Cl.
USPC ............................................... 607/116
(58) Field of Classification Search
USPC ............................................... 607/116
See application file for complete search history.

(56) References Cited

U.S. PATENT DOCUMENTS

| 6,567,703 | B1 | 5/2003 | Thompson et al. |
| 7,363,090 | B2 * | 4/2008 | Halperin et al. ............ 607/116 |
| 2004/0176817 | A1 | 9/2004 | Wahlstrand et al. |
| 2007/0217121 | A1 | 9/2007 | Fu et al. |
| 2009/0243756 | A1 * | 10/2009 | Stevenson et al. ........... 333/172 |
| 2009/0281592 | A1 * | 11/2009 | Vase ............................ 607/37 |

OTHER PUBLICATIONS

European Search Report dated May 6, 2011 (6 pages).

\* cited by examiner

*Primary Examiner* — Christopher D Koharski
*Assistant Examiner* — Philip Edwards
(74) *Attorney, Agent, or Firm* — Arc IP Law, PC; Joseph J. Mayo

(57) ABSTRACT

An electrode device for active medical implants that includes an elongated electrode body having a proximal end and a distal end, a tip contact pole on the distal end and/or a ring contact pole before the distal end, electrical supply leads to the tip and ring contact poles, and a high-frequency filter in at least one of the supply leads, which is composed of one or more electronic components (9) and is assigned to the tip and/or ring contact pole, wherein the electronic component(s) (9) are each designed as a miniature component using LTCC technology.

13 Claims, 4 Drawing Sheets

ELECTRODE DEVICE FOR ACTIVE MEDICAL IMPLANT

This application takes priority from German Patent Application DE 10 2010 000 372.7, filed 11 Feb. 2010, the specification of which is hereby incorporated herein by reference.

BACKGROUND OF THE INVENTION

1. Field of the Invention

Embodiments of the invention relate to an electrode device for active medical implants, which comprises an elongated electrode body having a proximal end and a distal end, a tip contact pole on the distal end and/or a ring contact pole before the distal end, electrical supply leads to the tip contact pole and the ring contact pole, and a high-frequency filter in at least one of the supply leads, which is composed of one or more electronic components and is assigned to the tip and/or ring contact pole.

2. Description of the Related Art

Regarding the background of the invention, it should be pointed out that the subject matter of one or more embodiments of the invention is relevant primarily in conjunction with cardiac pacemakers, implantable defibrillators, and other types of active implantable electromedical devices. The latter typically comprise at least one current/voltage-carrying supply lead in the electrode device—typically referred to simply as "electrode",—the distal end of which is disposed e.g. in a ventricle and is used to measure cardiological potential signals or to transmit relevant therapeutic current signals.

The compatibility of such electrode devices in the case of implantable electromedical devices having high-frequency magnetic fields of the type used in imaging diagnostic methods in particular which are based on magnetic resonance—so-called MRI (magnetic resonance imaging) methods—is a serious problem. In the case of such MRI methods, a magnetic alternating field pulsed with radio frequency (RF) is superimposed on a strong static magnetic field, which is used to change the energy status of the protons in the tissue being investigated and to produce corresponding MRI signals from the tissue.

Due to the laws of electromagnetic induction, this magnetic alternating field induces alternative voltages in the supply lead of the electrode devices—under discussion here—of electromedical device implants, the energy of which is converted to heat at the electrically conductive contact poles, in particular, of the electrode device with human tissue. This can result in considerable heating e.g. of the tip contact of a cardiac electrode with corresponding impairment and even damage of the cardiac tissue in contact therewith or that surrounds it.

To prevent these problems, U.S. Pat. No. 7,363,090 B2 proposes the use of filters on the basis of oscillating circuits of parallel-connected coil and capacitor, which is assigned to the corresponding supply lead for the tip contact pole or a ring contact pole of a corresponding electrode of an implantable electromedical device. The filters disclosed in that known patent are designed—in practical application by the patent owner—as relatively voluminous components that stiffen the electrode device along a certain length and impart unfavorable mechanical properties to the electrode equipped therewith. Furthermore, the filter is accommodated in a closed housing that does not provide passage for the guide wires that are typically used when implanting an electrode. To this extent, the potential uses of this known electrode with filter devices is limited.

Document US 2009/0281592 A1 makes known filter components for reducing the heating of pacemaker electrodes of an electromedical implant due to the effect of high-frequency magnetic fields produced during MRI procedures, in which case an induction coil is installed around a non-conductive central section of a shank which connects a tip contact pole to an inner spiral conductor of the electrode device. By installing an induction coil on the shank, inductive signal filtering is achieved to reduce the electrode tip without the need for a relatively long, voluminous coil body along the length of the electrode. Capacitive elements can also be integrated in the shank to create an LC filter circuit. As an alternative thereto, a so-called "air coil" is disclosed in this publication as an inductive element, in the case of which the shank may be omitted.

The filter devices according to the prior art typically result in excessive stiffening of the electrode device along a certain length. They are relatively complex and not very compact.

BRIEF SUMMARY OF THE INVENTION

Proceeding therefrom, the problem addressed by the invention is that of improving electrode devices for active medical implants such that the filter devices thereof are miniaturized to the greatest extent possible. This problem is solved by the features as claimed herein, according to which the electronic component(s) is/are designed as miniature components using LTCC technology.

Such LTCC components are made from low temperature cofired ceramics and are based on a technology for manufacturing multilayer circuits on the basis of sintered ceramic substrates. It is therefore possible, in principle, to create printed circuit boards, capacitors, resistors, and coils that are applied by screen printing or photochemical processes. The unfired ceramic foils are imaged individually and then stacked and laminated. Finally, a defined sintering profile is carried out with a peak temperature of approximately 850 to 900° C.

This technology combines the advantages of high temperature cofired ceramics technology and thick film technology. Primarily when item counts are small to moderate, it represents a low-cost alternative to conventional printed circuit board technology, which has favorable consequences in the field of medical engineering.

By using such LTCC components, a high scale of integration of the high-frequency filters manufactured therewith can be obtained, which is an extremely favorable aspect given their small size. Since the high-frequency filters are small, they stiffen the electrode device to a lesser extent than is the case with the conventional embodiment of these filter devices.

According to a preferred embodiment, the high-frequency filter can comprise a capacitor and/or a coil based on LTCC technology, wherein a capacitor can be integrated into a dielectric material as an LTCC component. A capacitor, as an LTCC component, can also be mounted on a dielectric material by soldering, welding, or bonding using a conductive adhesive.

If a ceramic dielectric is provided as the dielectric material, it is possible to implement an intrinsic capacitor (e.g. the sandwich of conductive material, nonconductive—i.e. having strong dielectric characteristics—material, conductive material, in the order listed, forms a capacitor).

A preferred embodiment of a coil based on LTCC technology uses a structure integrated directly into a ceramic substrate. This can be accomplished preferably by layering open metal rings and ceramic layers on top of one another in alternation, in the manner of a sandwich, wherein adjacent metal rings are electrically connected at their open ends by way of passages. It is therefore possible to create compact coils having sufficient inductance values.

It is also possible to design the coil as a planar coil on a flexible substrate. This has the advantage that the component can then be bent round, due to the flexibility of the substrate, and housed in the electronic assembly of the high-frequency filter in a space-saving manner. A particularly compact embodiment that uses a flexible substrate involves designing the coil as a spiral since the tracks are thus disposed in a plane. This concept can also be implemented in the form of a plurality of spirals on a flexible substrate. The latter can then be rolled up preferably to form a cylinder, thereby resulting in a configuration that is adapted in an optimal manner to installation in an electrode device.

BRIEF DESCRIPTION OF THE DRAWINGS

Further features, details, and advantages of the invention will be apparent from the following description which explains embodiments of the invention in greater detail. In the drawings.

DETAILED DESCRIPTION OF THE INVENTION

Figure 1:
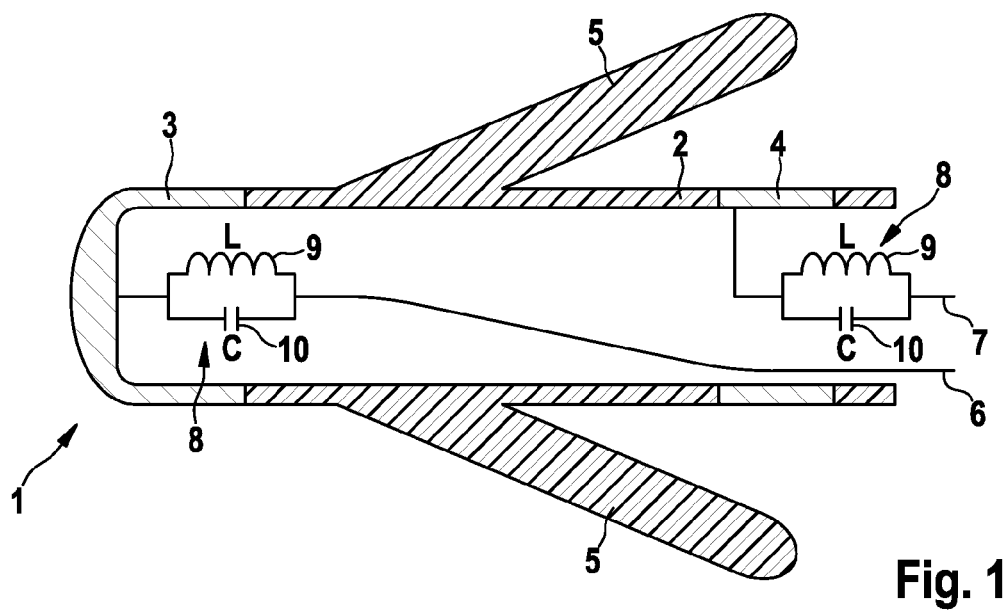
FIG. 1 shows a schematic longitudinal cross section of an electrode device in the distal end region thereof.

FIG. 1 shows the region of distal end 1 of an electrode device that comprises an elongated electrode body 2 composed of a flexible, insulating tube.

A tip contact pole 3, which is usually referred to as a tip electrode, is fastened to the tip of electrode body 2; when used in the electrode device, tip contact pole 3 is brought into contact with cardiac tissue, for example.

A ring contact pole 4 is fastened in electrode body 2, before tip contact pole 3 in the proximal direction, and at a distance therefrom; ring contact pole 4 is likewise used to output electrocardiological stimulating currents or to measure electrocardiological signals. A plurality of silicone anchors 5 for fastening the electrode device to a suitable point in the cardiac tissue project obliquely outward from electrode body 2 in the proximal direction between tip and ring contact poles 3, 4, respectively.

The electrical connection between an electromedical implant, such as a cardiac pacemaker, which is not shown in greater detail, and tip and ring contact poles 3, 4, respectively, is established by an electrical supply lead 6, 7, respectively, which is usually designed as a helix.

As depicted schematically as a type of block diagram in FIG. 1, a high-frequency filter 8 is connected into both supply leads 6, 7, and is formed by an LC oscillating circuit composed of a parallel connection of a coil 9 and a capacitor 10.

The electronic components that are coil 9 and capacitor 10 are each designed as miniature components using LTCC technology, as explained in detail at the beginning of the description. Reference is hereby made thereto, to prevent repetition.

Capacitor 10 can be integrated into a conventional SMD that is small. Sizes having the identifiers 0402, 0201 or 1005 are advantageous in this context. Capacitor 10 is integrated into dielectric material as an LTCC component. An alternative is to mount an LTCC capacitor 10 onto a dielectric material by soldering, welding, or bonding using conductive adhesive.

Figure 5A:
FIG. 5A shows a depiction of a cross section of an LTCC capacitor.

When a dielectric material is used as a ceramic dielectric, capacitor 10 can be implemented as an intrinsic capacitor. The volume of the capacitor can therefore be distributed within the entire electronic assembly of high-frequency filter 8, as shown for example in FIG. 5A of the cross section of an LTCC capacitor. Compartment-like structures 20 and 22 are the metallization layers inside LTCC substrate 21. Two adjacent metal layers, together with the ceramic substrate disposed therebetween, form a single capacitor.

Figure 5B:
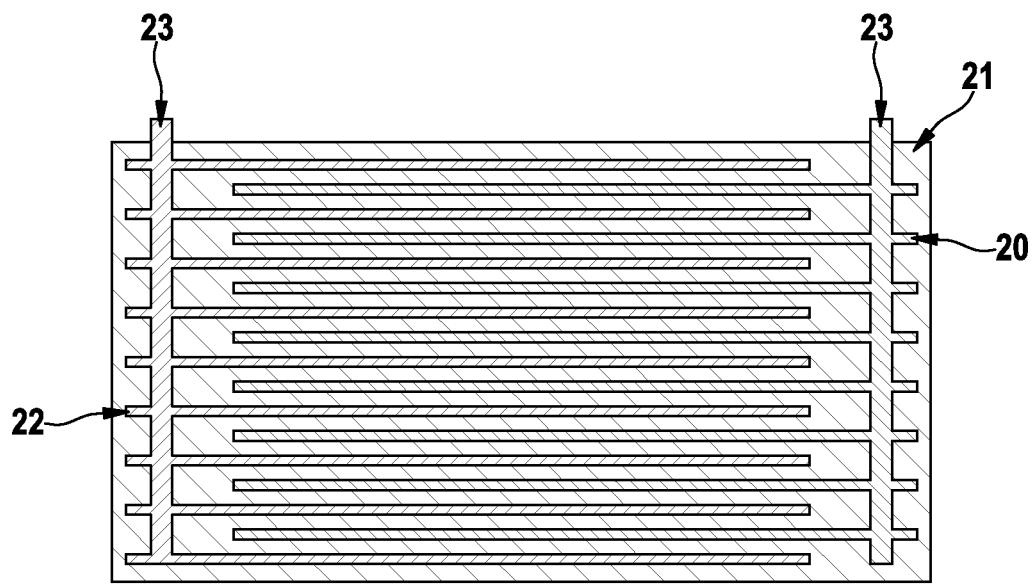
FIG. 5B shows a depiction of a cross section of an LTCC capacitor connected to passages.

As shown in FIG. 5B, the individual capacitors can be electrically interconnected such that they form one capacitor having greater capacitance. Electrical connections 23 between the individual layers are typically implemented as passages in LTCC technology. The following Figure shows one possible embodiment, in which the connections of the capacitor are routed on the surface.

In the special application of the capacitor as part of a filter, the connectors can also be connected directly to the coil or coils inside the substrate.

Figure 2:
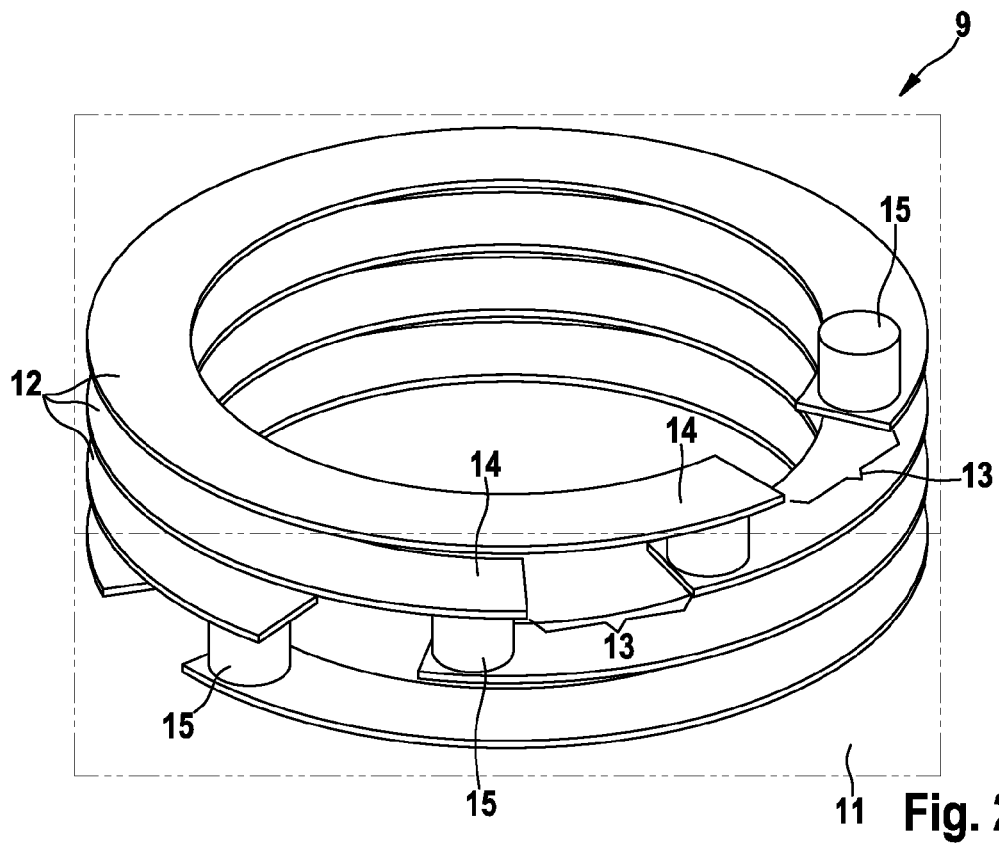
FIG. 2 shows a perspective view of the tracks of an LTCC coil.

The design of a coil 9 using LTCC technology is shown in FIG. 2. Such a coil 9 is integrated directly in a ceramic substrate 11 (shown as a dashed line in FIG. 2), by forming coil 9 by stacking open metal rings 12 and ceramic layers—which have been omitted for clarity—in alternation, one above the other, in the manner of a sandwich. Metal rings 12 are formed of flat material in the shape of annular disks, and are disposed parallel to one another, overlapping in the stacking direction. Gap 13 between open ends 14 of metal rings 12 extends by a few circumferential degrees around metal rings 12. Gaps 13 of adjacent metal rings 12 are offset from one another in the peripheral direction such that they do not overlap.

The electrical connection between individual metal rings 12 is established in each case using passages 15 in the form of short lead sections before the respective ends of metal rings 12.

Figure 3:
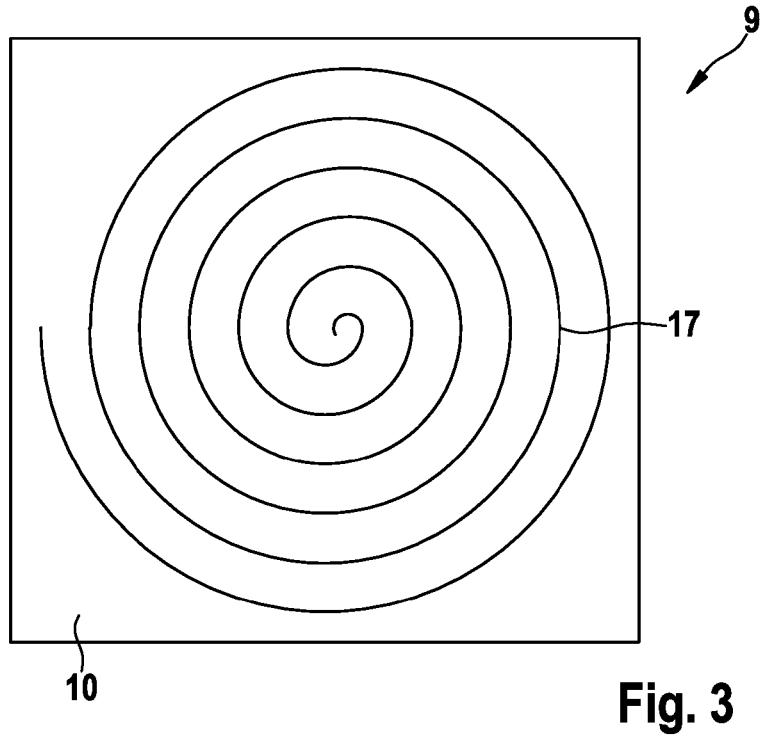
FIG. 3 shows a top view of an LTCC coil designed as a spiral.

An alternative embodiment of coil 9 is depicted in FIG. 3 in a highly schematic view. It is designed as a planar coil on a flexible substrate 16 by printing coil leads 17 as spirals on substrate 16. Due to the flexibility thereof, substrate 16 can be bent round, thereby enabling entire coil 9 to be integrated in the corresponding electronic component in a space-saving manner.

Figure 4A:
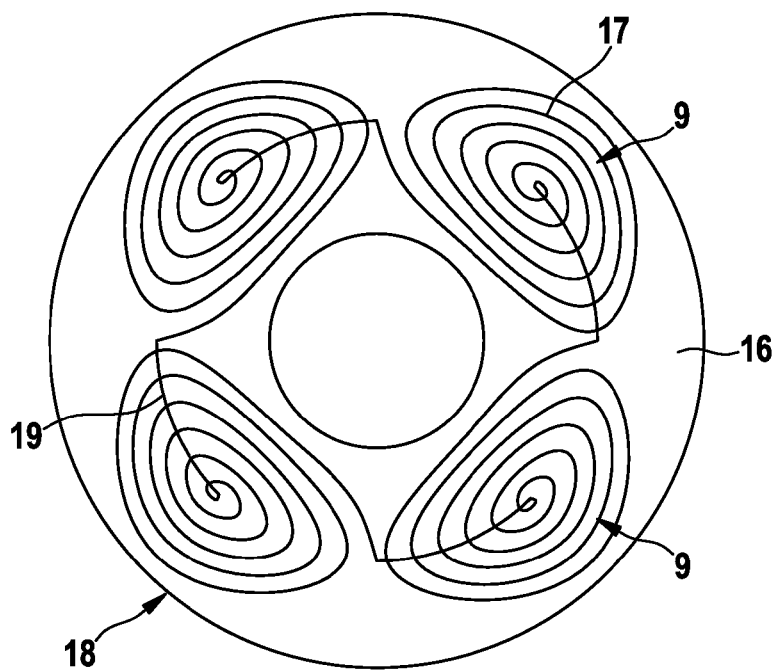
FIG. 4A shows a depiction of a coil cylinder having four coils installed in a spiral formation.
Figure 4B:
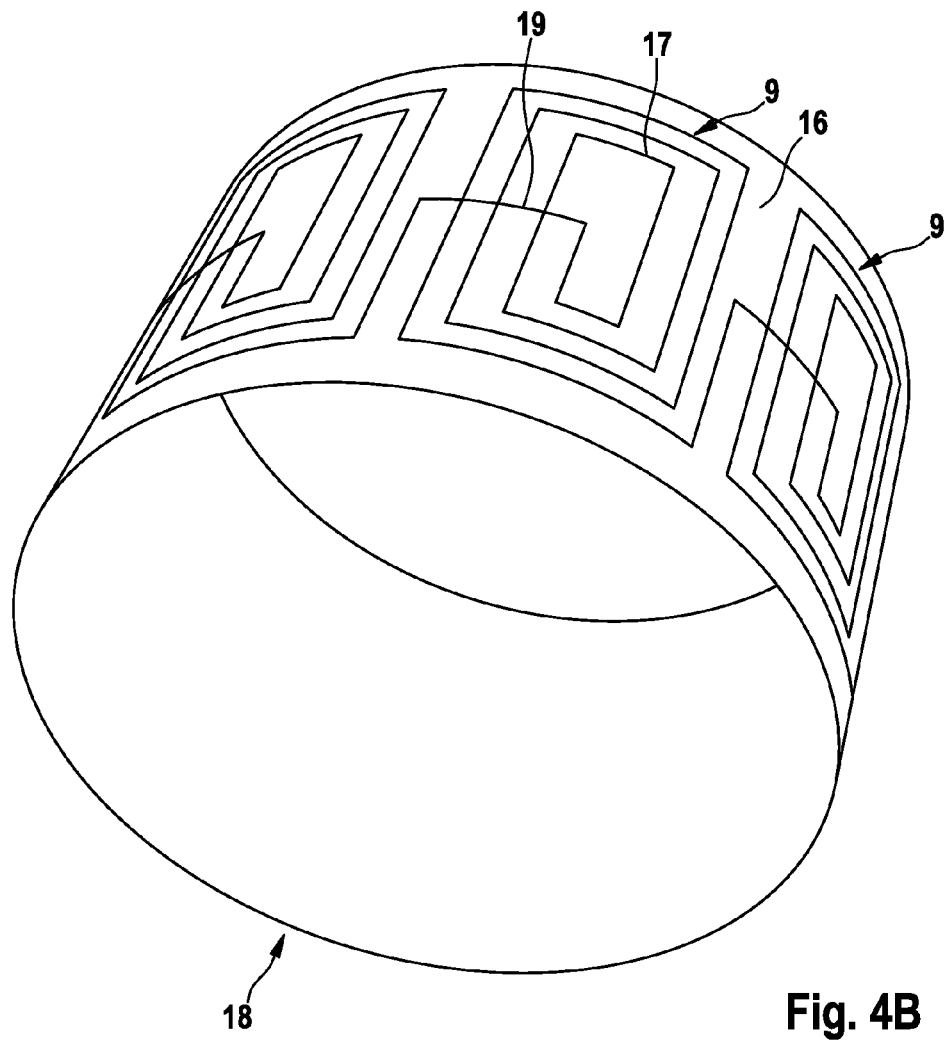
FIG. 4B shows a depiction of a coil cylinder having four coils installed in a spiral formation.

Finally, FIGS. 4A and 4B show the integration of four coils 9 in the form of spirals printed on a flexible substrate 16. Four coils 9 are connected in series, wherein the connection between the inner end of coil lead 17 and the outer start of the particular next coil 9 can be established by a straight connection lead 19 on the back side of flexible substrate 16. FIG. 4 shows four coils 9 on the substrate which has been wound to form a coil cylinder 18.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE CHARACTERS

1 Distal end
2 Electrode body
3 Tip contact pole
4 Ring contact pole
5 Silicone anchor
6 Supply lead
7 Supply lead
8 High-frequency filter
9 Coil
10 Capacitor
11 Substrate
12 Metal rings
13 Gap
14 Open end
15 Passage
16 Flexible substrate
17 Coil lead
18 Coil cylinder
19 Connecting line
20 Metallization layers in the LTCC
21 LTCC substrate
22 Metallization layers in the LTCC
23 Electrical connection

What is claimed is:

1. An electrode device for active medical implants, comprising:
   an elongated electrode body having a proximal end and a distal end;
   a tip contact pole on the distal end and/or a ring contact pole proximal to the distal end;
   electrical supply leads to the tip and ring contact poles;
   one or more electronic components;
   a high-frequency filter in at least one of the electrical supply leads, which comprises said one or more electronic components and is associated with the tip and/or ring contact pole; and,
   wherein the one or more electronic components comprises a miniature component comprising LTCC technology;
   wherein the high-frequency filter comprises a capacitor and/or a coil comprising LTCC technology;
      wherein the coil is configured as a sandwich composed of open metal rings and ceramic layers stacked on top of one another in alternation, wherein adjacent metal rings are electrically connected at their respective open ends by way of passages;
   wherein said metal rings are formed of flat material in the shape of annular disks, disposed parallel to one another and overlapping in a stacking direction; and
   wherein said metal rings overlapping in a stacking direction comprise one or more gaps between said open ends of said metal rings, which extend by a few circumferential degrees around said metal rings, and are offset from one another in the peripheral direction such that they do not overlap.

2. The electrode device according to claim 1, further comprising a capacitor configured as an LTCC component in dielectric material.

3. The electrode device according to claim 1, further comprising a capacitor that is mounted, as an LTCC component on a dielectric material with solder, or a weld, or a bond comprising conductive adhesive.

4. The electrode device according to claim 3, wherein said dielectric material comprises a ceramic dielectric configured to implement the capacitor as an intrinsic capacitor.

5. The electrode device according to claim 1, wherein the coil is integrated directly in a ceramic substrate.

6. The electrode device according to claim 1, wherein the coil is configured as a planar coil on a flexible substrate.

7. The electrode device according to claim 6, wherein the coil is configured as spirals on the flexible substrate.

8. The electrode device according to claim 7, wherein a plurality of said spirals are coupled to the flexible substrate.

9. The electrode device according to claim 8, wherein the flexible substrate comprises windings that form a cylinder.

10. The electrode device according to claim 9, wherein said cylinder is formed by a straight connection lead on the back side of said flexible substrate.

11. The electrode device according to claim 1, wherein the capacitor is integrated into a conventional surface-mounted device (SMD) with one or more size identifiers selected from the group comprising: 0402, 0201 or 1005.

12. The electrode device according to claim 1, wherein said passages for electrically connecting said adjacent metal rings comprise one or more electrical connections in the form of short lead sections before said respective ends of said adjacent metal rings in a stacked manner.

13. An electrode device for active medical implants, comprising:
   an elongated electrode body having a proximal end and a distal end;
   a tip contact pole on the distal end and/or a ring contact pole proximal to the distal end;
   electrical supply leads to the tip and ring contact poles;
   one or more electronic components;
   a high-frequency filter in at least one of the electrical supply leads, which comprises said one or more electronic components and is associated with the tip and/or ring contact pole;
   wherein the one or more electronic components comprises a miniature component comprising LTCC technology;
   wherein the high-frequency filter comprises a capacitor and/or a coil comprising LTCC technology;
      wherein the coil is integrated directly in a ceramic substrate;
      wherein the coil is configured as a sandwich composed of open metal rings and ceramic layers stacked on top of one another in alternation, wherein adjacent metal rings are electrically connected at their respective open ends by way of passages;
         wherein said passages for electrically connecting said adjacent metal rings comprise one or more electrical connections in the form of short lead sections before said respective ends of said adjacent metal rings in a stacked manner;
   wherein said metal rings are formed of flat material in the shape of annular disks, disposed parallel to one another and overlapping in a stacking direction;
   wherein said metal rings overlapping in a stacking direction comprise one or more gaps between said open ends of said metal rings, which extend by a few circumferential degrees around said metal rings, and are offset from one another in the peripheral direction such that they do not overlap.

* * * * *